United States Patent [19]

Sirrenberg et al.

[11] Patent Number: 4,757,086
[45] Date of Patent: Jul. 12, 1988

[54] N-BENZOYL-N'-(2,2,-DIFLUORO-3-METHYL-BENZO-1,4-DIOXANYL)-UREAS

[75] Inventors: Wilhelm Sirrenberg, Sprockhoevel; Albrecht Marhold, Leverkusen; Benedikt Becker, Mettmann, all of Fed. Rep. of Germany

[73] Assignee: Bayer Aktiengesellschaft, Leverkusen, Fed. Rep. of Germany

[21] Appl. No.: 762,980

[22] Filed: Aug. 6, 1985

[30] Foreign Application Priority Data

Aug. 24, 1984 [DE] Fed. Rep. of Germany ....... 3431219

[51] Int. Cl.[4] .................. A61K 31/335; C07D 319/20
[52] U.S. Cl. ...................................... 514/452; 549/362
[58] Field of Search ......................... 549/362; 574/452

[56] References Cited

U.S. PATENT DOCUMENTS 3,748,356 7/1973 Wellinga et al. ...................... 564/44
4,139,636 2/1979 Sirrenberg et al. .................. 564/44
4,533,676 8/1985 Sirrenberg et al. ................. 549/362

FOREIGN PATENT DOCUMENTS 0042533 12/1981 European Pat. Off. .
0093977 11/1983 European Pat. Off. .
0097862 1/1984 European Pat. Off. .
3223505 12/1983 Fed. Rep. of Germany ...... 549/362

Primary Examiner—Nicky Chan
Attorney, Agent, or Firm—Sprung Horn Kramer & Woods

[57] ABSTRACT

Novel insecticidally and acaricidally active compounds of the formula in which
$R^1$ is halogen or alkyl,
$R^2$ is hydrogen, halogen or alkyl,
$R^3$ is hydrogen or methyl, and
X is oxygen or sulphur.

Several of the intermediates are also new.

11 Claims, No Drawings

N-BENZOYL-N'-(2,2,-DIFLUORO-3-METHYL-BENZO-1,4-DIOXANYL)-UREAS

The present invention relates to new substituted 1-phenyl-3-benzoyl-(thio)ureas, several processes for their preparation and their use as agents for combating pests, in particular as insecticides and acaricides.

It is already known that certain benzoylureas have insecticidal properties (compare, for example, U.S. Pat. specification No. 4,139,636 or U.S. Pat. specification No. 3,748,356).

The new substituted 1-phenyl-3-benzoyl-(thio)ureas of the general formula (I)

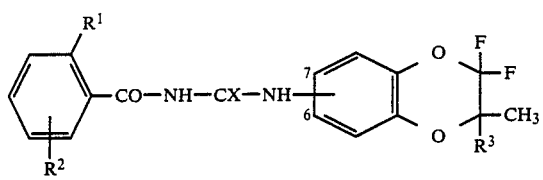

in which
R¹ represents halogen or alkyl,
R² represents hydrogen, halogen or alkyl,
R³ represents hydrogen or methyl and
X represents oxygen or sulphur,
have been found.

These new compounds have powerful biological, in particular insecticidal, properties which enable them to be used as agents for combating pests, in particular as insecticides and acaricides.

It has furthermore been found that the new substituted 1-phenyl-3-benzoyl-(thio)ureas of the general formula (I) are obtained by a process in which (a) substituted anilines of the general formula (II)

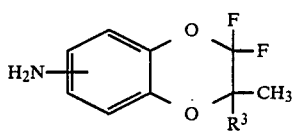

in which R³ has the abovementioned meaning,
are reacted with benzoyl iso(thio)cyanates of the general formula (III)

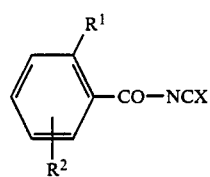

in which X, R¹ and R² have the abovementioned meanings,
if appropriate in the presence of a diluent, or (b) substituted phenyl iso(thio)cyanates of the general formula (IV)

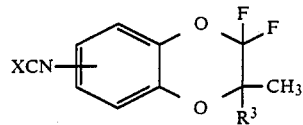

in which X and R³ have the abovementioned meanings, are reacted with benzoic acid amides of the general formula (V)

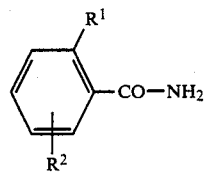

in which R¹ and R² have the abovementioned meaning, if appropriate in the presence of a catalyst and if appropriate in the presence of a diluent.

Alkyl R¹ and R² denotes straight-chain or branched alkyl with 1 to 6, preferably 1 to 4 and in particular 1 or 2, carbon atoms. Examples which may be mentioned are methyl, ethyl, n-propyl, i-propyl, n-butyl, i-butyl, sec.-butyl and tert.-butyl.

Halogen denotes fluorine, chlorine, bromine and iodine, preferably fluorine, chlorine and bromine and in particular fluorine or chlorine.

The radical R² is preferably in the 6-position of the phenyl ring.

In the general formulae (I), (II) and (IV), the benzodioxene radical is preferably bonded to the urea grouping or the NH₂ or NCX groups in the 6- or 7-position. The corresponding compounds can also be present in the form of mixtures of the compounds in which the benzodioxane radical is bonded in the 6- and 7-position.

The new compounds of the general formula (I) have properties which enable them to be used as agents for combating pests, and in particular they are distinguished by an outstanding insecticidal and acaricidal activity.

The invention preferably relates to new compounds of the general formula (I) in which
X represents oxygen or sulphur,
R¹ represents halogen or $C_1$-$C_6$-alkyl,
R² represents hydrogen, halogen or $C_1$-$C_6$-alkyl and
R³ represents hydrogen or methyl.

Particularly preferred compounds of the general formula (I) are those in which
X represents oxygen or sulphur,
R¹ represents fluorine, chlorine, bromine or $C_1$-$C_4$-alkyl,
R² represents hydrogen, fluorine, chlorine, bromine or $C_1$-$C_4$-alkyl and
R³ represents hydrogen or methyl.

Especially preferred compounds of the general formula I are those in which
X represents oxygen or sulphur,
R¹ represents fluorine or chlorine,
R² represents fluorine or chlorine in the 6-position and
R³ represents methyl.

If 2,2-difluoro-3,3-dimethyl-6-amino-1,4-benzodioxene and 2-chlorobenzoyl isocyanate are used as starting substances in process variant (a), the course of the reaction can be represented by the following equation:

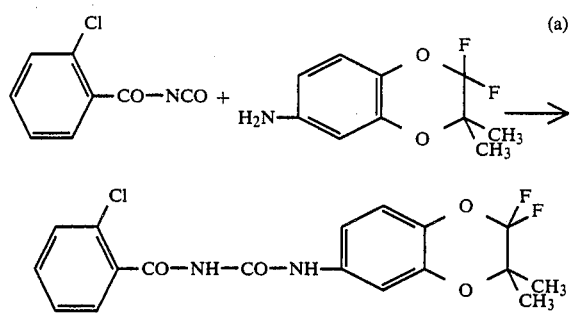

(a)

If 2,2-difluoro-3,3-dimethyl-1,4-benzodioxene 6-isocyanate and 2-chlorobenzamide are used as starting substances in process variant (b), the course of the reaction can be represented by the following equation:

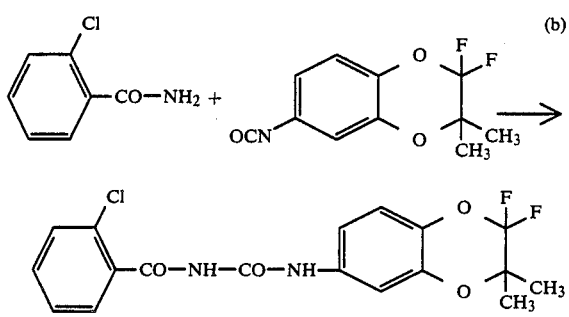

(b)

The starting compounds of the general formulae (II) and (IV) are new. Their preparation processes are described below.

The starting compounds of the formula (III) are known or can be obtained by generally known methods.

Examples which may be mentioned of the compounds of the general formula (III) are: 2-fluoro-, 2-chloro-, 2-bromo-, 2-methyl-, 2,6-difluoro-, 2,6-dichloro-, 2-chloro-6-fluoro-, 2-chloro-4-methyl, 2,6-difluoro-, 2,4-dichloro- and 2,6-dimethyl-benzoyl isocyanate and -benzoyl isothiocyanate.

The starting compounds of the general formula (V) are known or can be obtained by generally known methods.

Examples which may be mentioned of the compounds of the formula (V) are: 2-fluoro-, 2-chloro-, 2-bromo-, 2-methyl-, 2,6-difluoro-, 2,6-dichloro-, 2-chloro-6-fluoro-, 2-chloro-4-methyl, 2,4-difluoro-, 2,5-dichloro- and 2,6-dimethyl-benzoic acid amide.

Possible diluents in process variants (a) and (b) are virtually all the inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylacetamide and N-methyl-pyrrolidone, and tetramethylene sulphone.

Catalysts which can be used for the reaction according to process variant (b) are, preferably, tertiary amines, such as triethylamine and 1,4-diazabicyclo-[2,2,2]-octane, and organic tin compounds, such as, for example, dibutyl-tin dilaurate. However, the process can also be carried out without such catalysts.

The reaction temperature can be varied within a substantial range in both process variants. In general, process variant (a) is carried out between 20° and 180° C., preferably between 40° to 120° C., and process variant (b) is carried out between 20° and 200° C., preferably between 60° and 190° C. The process variants according to the invention are in general carried out under normal pressure.

The starting substances are usually employed in approximately equimolar amounts for carrying out the process variants according to the invention. An excess of one or the other of the reaction components provides no substantial advantages.

The reaction products are worked up by customary methods, for example by filtering off the precipitated product with suction or by dissolving undesirable by-products out of the reaction mixture. They are characterized by their melting point.

The compounds of the general formulae (II) and (IV) are new. They can be summarized by the general formula (VI):

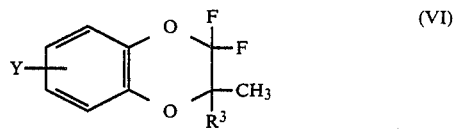

(VI)

in which
Y represents NH$_2$ or NCX,
wherein
X denotes oxygen or sulphur, and
R$^3$ represents hydrogen or methyl.

These compounds and processes for their preparation are part of the present invention.

The compounds of the general formula (II)

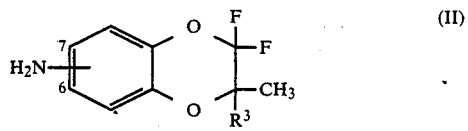

(II)

in which R$^3$ represents hydrogen or methyl,
are obtained by a process in which the compounds of the general formula (VII)

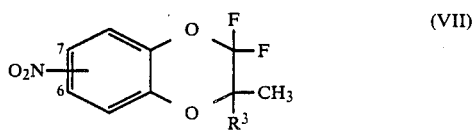

(VII)

in which R$^3$ has the abovementioned meaning,
are reduced in the customary manner, preferably by catalytic hydrogenation or with the aid of metals or metal salts.

The position isomers can be separated and isolated by the customary separation methods, preferably by distillation.

The following isomers can be obtained in this manner: 2,2-difluoro-3,3-dimethyl-6-amino-1,4-benzodioxene, 2,2-difluoro-3,3-dimethyl-7-amino-1,4-benzodioxene, 2,2-difluoro-3,3-dimethyl-5-amino-1,4-benzodioxene, 2,2-difluoro-3,3-dimethyl-8-amino-1,4-benzodioxene, 2,2-difluoro-3-methyl-6-amino-1,4-benzodioxene, 2,2-difluoro-3-methyl-7-amino-1,4-benzodioxene, 2,2-difluoro-3-methyl-5-amino-1,4-benzodioxene and 2,2-difluoro-3-methyl-8-amino-1,4-benzodioxene.

The compounds of the general formula (IV) are obtained from the resulting compounds of the general formula (II) by reaction with phosgene or thiophosgene in the customary manner.

All the customary catalysts can be used for the catalytic hydrogenation of the nitro compounds of the general formula (VII), such as Raney nickel, platinum, platinum oxide and palladium, it also being possible for the catalysts to be present on supports, for example active charcoal or aluminum oxide.

Possible solvents are all the solvents usually employed for hydrogenation reactions, such as alcohols, for example methanol, hydrocarbons, such as toluene, or ethers, for example dioxane and tetrahydrofuran.

Increased hydrogen pressures, preferably between 10 and 80 bar, are in general employed. The hydrogenation is preferably carried out at temperatures from 10 to 100, in particular 20° to 80° C. Working up and isolation of the compounds of the general formula (II) are effected in the customary manner.

The reduction of the nitro compounds of the general formula (VII) can also be carried out in the customary manner with metals, such as iron and tin, and salts thereof, preferably $SnCl_2$. The reduction with $SnCl_2$ is preferably carried out in a mixture of aqueous HCl and dioxane (or under anhydrous conditions, in alcohols, such as ethanol), at temperatures between 20° and 100° C. Analogously, it is also possible to use iron in the form of iron powder or iron fillings, temperatures of 80° to 100° C. preferably being employed. Working up and isolation of the compounds of the general formula (II) are in this case also effected in the customary manner.

The compounds of the general formula (IV) can easily be obtained from the compounds of the general formula (II) and phosgene or thiophosgene by the customary phosgenation methods. The solvents used are preferably optionally halogenated aromatic or araliphatic solvents, such as chlorotoluene, toluene or xylene.

The phosgenation is preferably carried out at temperatures between 0° and 150°, preferably between 0° and 130° C.

The compounds of the general formula (IV) are worked up and isolated by generally customary methods.

The preparation of the compounds of the general formula (VII) employed as starting materials is described in the experimental section.

The active compounds are well tolerated by plants, have a favorable level of toxicity to warm-blooded animals, and are suitable for combating animal pests, especially insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp.. From the order of the Anoplura, for example, *Phylloxera vastatrix*, Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus Ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Eusceliis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.. From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating undesirable pests in the field of livestock husbandry and stock breeding, it being possible, by combating the pests, to achieve better results, for example higher milk yields, higher weight, a more attractive animal coat, a longer life and the like.

The active compounds according to the invention are used in these fields in a known manner, such as by external application in the form of, for example, dipping, spraying and pouring on and spotting on.

The preparation of the compounds of the formula (I) according to the invention may be illustrated by the following preparation examples (ratio data and percent data relate to weight ratios and percentages by weight):

EXAMPLE 1

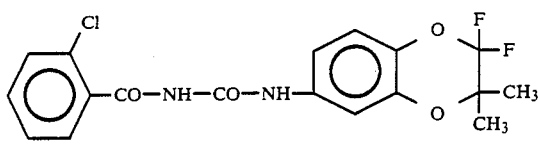

2.15 g (0.01 mole) of 2,2-difluoro-3,3-dimethyl-6-amino-1,4-benzodioxene are dissolved in 40 ml of dry toluene. A solution of 1.82 g (0.01 mole) of 2-chlorobenzoyl isocyanate in 10 ml of dry toluene is added dropwise at 60° C. The mixture is stirred at 80° C. and 0.5 hour and is then cooled to room temperature. After addition of a little petroleum ether, the precipitate formed is filtered off with suction. 3.2 g (yield: 80.5% of theory) of 1-(2,2-difluoro-3,3-dimethyl-benzo-1,4-dioxen-6-yl)-3-(2-chlorobenzoyl)-urea of melting point 176° C. are obtained.

The compounds of the following examples can be prepared analogously to Example 1 (since the starting compounds employed are mixtures of 6- and 7-amines, the compounds of the following examples are mixtures of the 6- and 7-isomers):

$$\text{(I)}$$

R$^1$—[phenyl]—CO—NH—CX—NH—[benzodioxene with O, F, F, R$^3$, CH$_3$]
R$^2$

| Example No. | R$^1$ | R$^2$ | R$^3$ | X | Melting point (°C.) of 6-isomer | Yield (% of theory) |
|---|---|---|---|---|---|---|
| 2 | Cl | 6-F | CH$_3$ | O | 185 | 67.5 |
| 3 | F | 6-F | CH$_3$ | O | 185 | 65.5 |
| 4 | Cl | 6-F | CH$_3$ | S | 211 | 79.0 |
| 5 | Br | H | CH$_3$ | S | 171 | 74.5 |
| 6 | F | 6-F | CH$_3$ | S | 211 | 91.5 |
| 7 | Cl | 6-Cl | CH$_3$ | S | 204 | 71.5 |
| 8 | Cl | 4-F | CH$_3$ | O | 210 | 91.0 |
| 9 | Cl | 4-F | CH$_3$ | S | 190 | 69.5 |
| 10 | CH$_3$ | H | CH$_3$ | S | 140 | 69.0 |

The preparation of the compounds of the general formulae (II) and (IV) according to the invention may be illustrated with the aid of the following examples:

EXAMPLE 1A

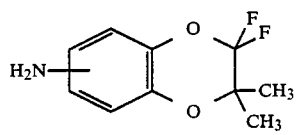

A mixture of 75 g of 2,2,-difluoro-3,3-dimethyl-6-nitro-1,4-benzodioxene and 2,2-difluoro-3,3-dimethyl-7-nitro-1,4-benzodioxene (ratio of 80.5:19.5) is hydrogenated in 400 ml of methanol in the presence of 10 g of Raney nickel at 25°–45° C. under a hydrogen pressure of 10–50 bar until the uptake of hydrogen has ended. After the catalyst has been removed by filtration and the methanol has been distilled off, the amine mixture is distilled (boiling point: 90°–5° C./0.3 mbar, n$_D^{25}$: 1.5150), yield: 55 g.

The mixture can be separated by preparative gas chromatography. According to spectroscopic findings, the main component is the 6-amino isomer.

7-Amino-2,2-difluoro-3,3-dimethyl-1,4-benzodioxene, boiling point: 72°–5° C./0.05 mbar, n$_D^{20}$: 1.5142.

6-Amino-2,2-difluoro-3,3-dimethyl-1,4-benzodioxene, boiling point: 118°–20° C./1.5 mbar, melting point: 54°–6° C.

EXAMPLE 2A

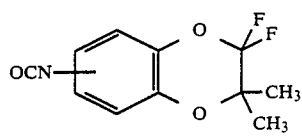

50 g of 2,2-difluoro-3,3-dimethyl-6-amino-1,4-benzodioxene (80% pure with a 7-amino isomer content of 20%) are introduced into 500 ml of dry chlorobenzene at ~0°–5° C., and about 40 g of phosgene are passed in. The temperature is then increased continuously during the phosgenation up to a final temperature of 130° C. The mixture is then blown out with nitrogen and subsequently subjected to fractional distillation. 48 g of 2,2-difluoro-3,3-dimethyl-6-isocyanato-1,4-benzodioxene (80% pure with a 7-isocyanato isomer content of 20%) are obtained, boiling point: 80°–5° C./0.25 mbar.

EXAMPLE 3A

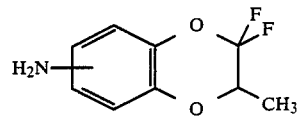

Analogously to Example 1A, 39 g of amino compound of corresponding isomer purity, boiling point: 84°–88° C./0.2 mbar, are obtained from 50 g of 2,2-difluoro-3-methyl-6-nitro-1,4-benzodioxene (62% pure+7-nitro isomer content).

6-Amino-2,2-difluoro-3-methyl-1,4-benzodioxene, boiling point: 86°–90° C./0.5 mbar, melting point: 48° C., from cyclohexane.

7-Amino-2,2-difluoro-3-methyl-1,4-benzodioxene, boiling point: 80°–2° C./0.4 mbar, n$_D^{20}$: 1.5130.

EXAMPLE 4A

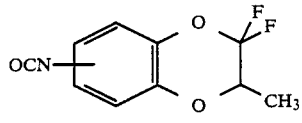

30 g of phosgene are condensed in 200 ml of dry chlorobenzene at 0°–10° C. and 30 g of 2,2-difluoro-3-methyl-6-amino-1,4-benzodioxene (62% pure+7-amino isomer content) in 50 ml of chlorobenzene are then added dropwise, while passing in further phosgene. After the end of the addition, the phosgenation is continued at a temperature rising to 130° C. and the mixture is then blown out with nitrogen and distilled. Boiling point: 78°–81° C./0.3 mbar.

The starting compounds of the general formula (VII) can be prepared according to the following examples:

EXAMPLE 1B

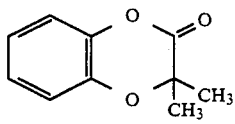

70 g of potassium carbonate and 55 g of pyrocatechol are initially introduced into 250 ml of acetonitrile and the mixture is heated to 50° C. 100 g of methyl bromoisobutyrate are then added dropwise and the mixture is boiled under reflux and stirred for 5 hours. After the acetonitrile has been distilled off, 200 ml of water are added to the residue which remains and the mixture is rendered acid with hydrochloric acid and extracted with methylene chloride. 74 g of 2,2-dimethyl-benzodioxen-3-one with a boiling point of 115° to 120° C. under 14 mbar and a melting point of 42° to 44° C. are obtained from the extract by distillation.

EXAMPLE 2B

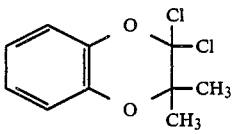

115 g of 2,2-dimethyl-benzodioxen-3-one, obtained according to Example 1B, are mixed with 172 g of phosphorus pentachloride and the mixture is heated to the reflux temperature, with stirring. At 65° C., the mixture becomes liquid, and the reflux temperature is reached at 120° C. After 2 hours, the phosphorus oxychloride formed is distilled off and the crude product is subjected to distillation. 128 g of 2,2-dimethyl-3,3-dichloro-benzodioxene with a boiling point of 132° to 140° C. under 20 mbar and a melting point of 63° to 64° C. (recrystallized from hexane) are obtained.

EXAMPLE 3B

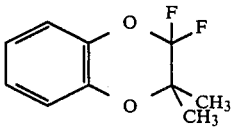

128 g of 2,2-dimethyl-3,3-dichloro-benzodioxene, obtained according to Example 2B, are initially introduced into a stainless steel fluorination apparatus, and 250 ml of hydrogen fluoride are metered in at −10° C. The temperature is slowly increased to +10° C., with stirring, and the mixture is finally warmed to 20° C. It is stirred until no further evolution of hydrogen chloride is to be observed (about 4 hours). The excess hydrogen fluoride is then distilled off and 83 g of 2,2-dimethyl-3,3-difluoro-benzodioxene with a boiling point of 84° to 86° C. under 22 mbar and a refractive index $n_D^{20}$ of 1.4740 are subsequently obtained.

EXAMPLE 4B

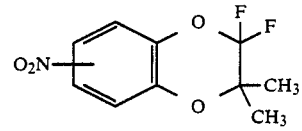

70 g of 2,2-difluoro-3,3-dimethyl-1,4-benzodioxene are taken at 5° C. and a mixture of 53 ml of nitric acid (65% strength) and 60 ml of concentrated sulphuric acid is added dropwise. The mixture is then stirred at 10° C. for 1 hour and at 20° C. for 1 hour. After the mixture has been discharged onto ice, the phases are separated with methylene chloride and the organic phase is washed with water, dried and distilled. 76 g of the nitro compound (boiling point: 95°–100° C./0.2 mbar, $n_D^{20}$: 1.5205), in which the content of the 6-nitro isomer is 80.5%, are obtained.

The starting compounds in which $R^3$ represents hydrogen are prepared analogously.

The biological activity of the compounds of the general formula (I) according to the invention may be illustrated by the following biological example:

EXAMPLE A

Plutella Test

Solvent: 15 parts by weight of dimethylformamide
Emulsifier: 1 part by weight of alkylaryl polyglycol ether To produce a suitable preparation of active compound, 1 part by weight of active compound is mixed with the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*), as long as the leaves are still moist.

After the specified period of time, the destruction in % is determined. 100% means that all the caterpillars have been killed; 0% means that none of the caterpillars have been killed.

At an active compound concentration of 0.1%, for example, the compounds of Examples 1 to 6 exhibited a destruction of 100% after 7 days.

It will be understood that the specification and examples are illustrative but not limitative of the present invention and that other embodiments within the spirit and scope of the invention will suggest themselves to those skilled in the art.

What is claimed is:
1. A mixture of compounds of the formula

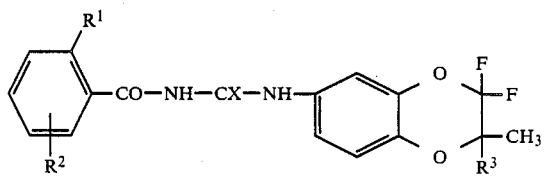

and

-continued

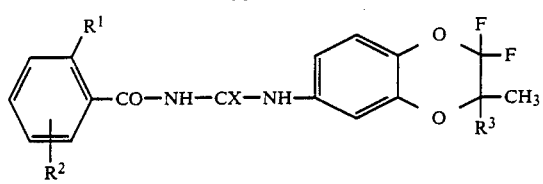

in which

R¹ is halogen or alkyl,

R² is hydrogen, halogen or alkyl,

R³ is hydrogen or methyl, and

X is oxygen or sulphur.

2. A mixture according to claim 1, in which

R¹ is halogen or $C_1$–$C_6$-alkyl, and

R² is hydrogen, halogen or $C_1$–$C_6$-alkyl.

3. A mixture according to claim 1, in which

R¹ is fluorine, chlorine, bromine or $C_1$–$C_4$-alkyl, and

R² is hydrogen, fluorine, chlorine, bromine or $C_1$–$C_4$-alkyl.

4. A mixture according to claim 1, in which

R¹ is fluorine or chlorine,

R² is 6-F or 6-Cl, and

R³ is methyl.

5. A mixture according to claim 1, wherein such mixture is 1-(2,2difluoro-3,3-dimethyl-benzo-1,4-dioxen-6- and 7-yl)-3-(2-chloro-6-fluoro-benzoyl)-urea of the formulas

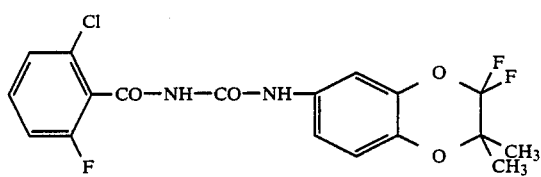

and

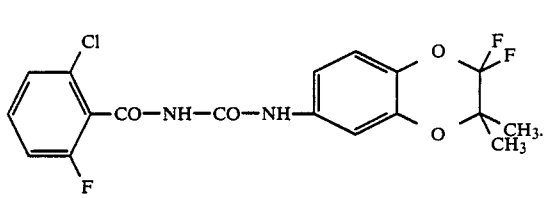

6. A mixture according to claim 1, wherein such mixture is 1-(2,2-difluoro-3,3-dimethyl-benzo-1,4-dioxen-6- and 7-yl)-3-(2,6-difluoro-benzoyl)-urea of the formulas

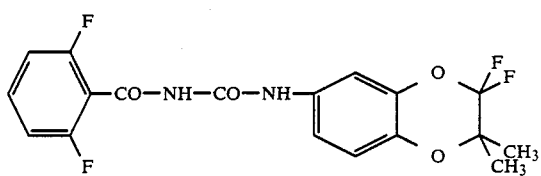

and

-continued

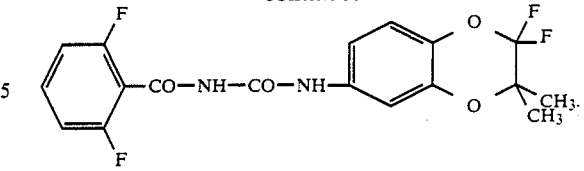

7. A mixture according to claim 1, wherein such mixture is 1-(2,2-difluoro-3,3-dimethyl-benzo-1,4-dioxen-6- and 7-yl)-3-(2-chloro-6-fluoro-benzoyl)-thiourea of the formulas

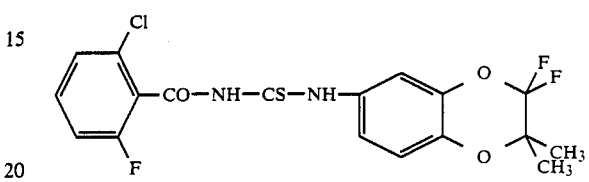

and

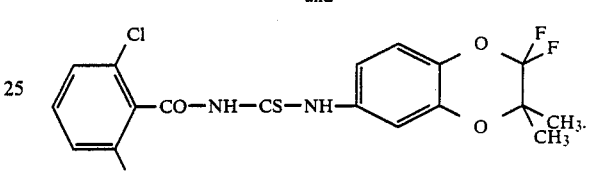

8. A mixture according to claim 1, wherein such mixture is 1-(2,2-difluoro-3,3-dimethyl-benzo-1,4-dioxen-6- and 7-yl)-3-(2,6-difluoro-benzoyl)-thiourea of the formulas

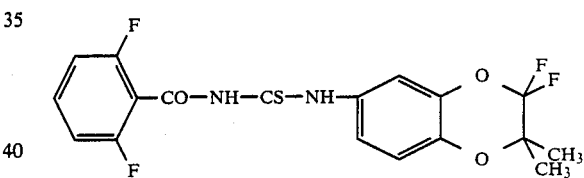

and

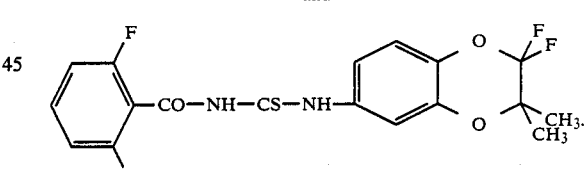

9. An insecticidal and acaricidal composition comprising an insecticidally and acaricidally effective amount of a mixture according to claim 1 in admixture with a diluent.

10. A method of combating insects and acarids which comprises applying to such insects or acarids or to an insect or acarid habitat an insecticidally or acaricidally effective amount of a mixture according to claim 1.

11. The method according to claim 10, wherein such mixture is 1-(2,2-difluoro-3,3-dimethyl-benzo-1,4-dioxen-6- and 7-yl)-3-(2-chloro-6-fluoro-benzoyl)-urea, 1-(2,2-difluoro-3,3-dimethyl-benzo-1,4-dioxen-6- and 7-yl)-3-(2,6-difluoro-benzoyl)-urea, 1-(2,2-difluoro-3,3-dimethyl-benzo-1,4-dioxen-6- and 7-yl)-3-(2-chloro-6-fluoro-benzoyl)-thiourea or 1-(2,2-difluoro-3,3-dimethyl-benzo-1,4-dioxen-6- and 7-yl)-3-(2,6-difluoro-benzoyl)-thiourea.

* * * * *